(12) United States Patent
Locke et al.

(10) Patent No.: US 12,042,360 B2
(45) Date of Patent: Jul. 23, 2024

(54) TRANSPARENT PEEL AND PLACE DRESSING FOR NEGATIVE-PRESSURE THERAPY

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 69 days.

(21) Appl. No.: 17/442,815

(22) PCT Filed: Apr. 21, 2020

(86) PCT No.: PCT/IB2020/053782
§ 371 (c)(1),
(2) Date: Sep. 24, 2021

(87) PCT Pub. No.: WO2020/217179
PCT Pub. Date: Oct. 29, 2020

(65) Prior Publication Data
US 2022/0168493 A1  Jun. 2, 2022

Related U.S. Application Data

(60) Provisional application No. 62/836,914, filed on Apr. 22, 2019.

(51) Int. Cl.
*A61F 13/05* (2024.01)
*A61M 1/00* (2006.01)

(52) U.S. Cl.
CPC .............. *A61F 13/05* (2024.01); *A61M 1/85* (2021.05); *A61M 1/915* (2021.05); *A61M 1/92* (2021.05); *A61M 1/96* (2021.05)

(58) Field of Classification Search
CPC ........ A61F 13/00068; A61F 2013/0054; A61F 13/01029; A61F 13/02; A61F 2013/51147;
(Continued)

(56) References Cited

U.S. PATENT DOCUMENTS 1,355,846 A  10/1920 Rannells
2,547,758 A   4/1951 Keeling
(Continued)

FOREIGN PATENT DOCUMENTS

AU   550575 B2   3/1986
AU   745271 B2   3/2002
(Continued)

OTHER PUBLICATIONS

Chinese Office Action for Corresponding Application No. 2020800287753, mailed May 31, 2022.
(Continued)

*Primary Examiner* — Kai H Weng
*Assistant Examiner* — Nhu Q. Tran

(57) ABSTRACT

A dressing for treating a tissue site with negative pressure may comprise a first polymer film having a plurality of fluid restrictions, and a second polymer film comprising a plurality of standoffs disposed adjacent to the first polymer film. The first polymer film and the second polymer film may be substantially transparent to allow observation of the tissue site. In some embodiments, at least some of the standoffs may be offset from the fluid restrictions. The second polymer film may comprise fluid passages adjacent to the standoffs in some examples.

20 Claims, 11 Drawing Sheets

(58) Field of Classification Search
CPC ........... A61F 2013/51322; A61M 1/85; A61M 1/915; A61M 1/92; A61M 1/96; A61M 1/90; A61M 1/916; A61M 1/71
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,213,992 B1* | 4/2001 | Dreier ................ A61F 13/42 |
| | | 604/385.01 |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0227969 A1* | 9/2009 | Jaeb ................ A61M 1/78 |
| | | 604/313 |
| 2010/0305490 A1* | 12/2010 | Coulthard ........... A61F 13/0206 |
| | | 604/313 |
| 2014/0163491 A1 | 6/2014 | Schuessler et al. |
| 2014/0249495 A1* | 9/2014 | Mumby ............. A61F 13/0223 |
| | | 604/385.01 |
| 2015/0080788 A1 | 3/2015 | Blott et al. |
| 2016/0022885 A1 | 1/2016 | Dunn et al. |
| 2016/0120706 A1* | 5/2016 | Collinson ............ A61M 1/913 |
| | | 604/319 |
| 2016/0144084 A1* | 5/2016 | Collinson ............... A61L 15/42 |
| | | 604/319 |
| 2018/0353339 A1 | 12/2018 | Locke et al. |
| 2018/0353342 A1* | 12/2018 | Locke ................ A61F 13/0206 |
| 2018/0353662 A1 | 12/2018 | Locke et al. |
| 2018/0353663 A1 | 12/2018 | Locke et al. |
| 2020/0038006 A1* | 2/2020 | Quintero ................ A61F 13/02 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |

(56) References Cited

FOREIGN PATENT DOCUMENTS

| | | |
|---|---|---|
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2013007973 A2 | 1/2013 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

International Search Report and Written Opinion for Corresponding Application No. PCT/IB2020/053782, mailed Aug. 10, 2020.

Japanese Notice of Rejection for corresponding application 2021-560861, dated Apr. 2, 2024.

\* cited by examiner

TRANSPARENT PEEL AND PLACE DRESSING FOR NEGATIVE-PRESSURE THERAPY

TECHNICAL FIELD

The invention set forth in the appended claims relates generally to tissue treatment systems and more particularly, but without limitation, to a transparent dressing for negative-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating a tissue site in a negative-pressure therapy environment are set forth in the appended claims. Illustrative embodiments are also provided to enable a person skilled in the art to make and use the claimed subject matter.

For example, in some embodiments, a dressing may comprise a thin, flexible, and transparent manifold material, which can facilitate treatment with negative pressure and also allow a tissue site to be observed during treatment. In some examples, the dressing may comprise a laminated structure with a transparent manifolding means and a fenestrated interface layer. Additionally or alternatively, the interface layer may be embossed or textured to provide more than one layer of manifolding and also provide a means for providing micro-strain to a tissue site. In some embodiments, the structure may be bonded or fused together by various means, including the use of an adhesive, welding, or heat-bonding where heat is applied to flame-laminate layers together.

In some embodiments, the manifold material may be formed from a polyurethane film that is vacuum-formed with an array of standoffs. Spacing between the standoffs may be varied, and may be increased to facilitate manifolding and optical transparency. Additionally or alternatively, the material between the standoffs may be perforated in some examples. For example, in some embodiments, a heat-perforation process can form small holes (about 1 millimeter) in the material. In other examples, a smaller number of larger perforations may be formed. The dressing may additionally include a fluid-impermeable cover having an aperture or fluid port, and a spacer material may be disposed between the manifold material and the cover to prevent the manifold material from being drawing or pushed into the aperture or fluid port during treatment.

Some examples may additionally include a fully or partially optically occlusive, highly-breathable polyurethane or other film cover, which may be removed to observe the tissue site through the dressing. For example, a screen layer may be assembled to the top cover and coated with a re-sealable adhesive, such as a pattern-coated silicone or polyurethane gel that would be highly breathable and allow the screen to be removed and replaced as desired for observing a tissue site through the other layers.

In some embodiments, the dressing may additionally include other materials that may be beneficial for protein and/or bacterial binding. For example, the primary interface layer may be made from a material such as polyurethane, which may be unlikely to bind with protein, and the primary manifold layer may be made from a material or coated with a material that can bind and retain bacteria.

More generally, a dressing for treating a tissue site with negative pressure may comprise a first polymer film having a plurality of fluid restrictions, and a second polymer film comprising a plurality of standoffs disposed adjacent to the first polymer film. The first polymer film and the second polymer film may be substantially transparent to allow observation of the tissue site. In some embodiments, at least some of the standoffs may be offset from the fluid restrictions. The second polymer film may comprise fluid passages adjacent to the standoffs in some examples.

Alternatively, other example embodiments may comprise a cover and a tissue interface, wherein the tissue interface comprises a first layer, a second layer, and a third layer. The first layer may comprise a plurality of standoffs and at least one fluid passage. The second layer may comprise a plurality of fluid restrictions. The third layer may comprise a plurality of apertures, and in some examples may include a treatment aperture. The cover, the first layer, the second layer, and the third layer may be assembled in a stacked relationship with the first layer and the second layer disposed between the cover and the third layer. At least some of the fluid restrictions may be exposed through the treatment aperture, and the cover may have an aperture that is fluidly coupled to at least one fluid passage in the first layer. The standoffs can be disposed adjacent to the second layer. In some examples, the treatment aperture may form a frame around at least some of the fluid restrictions. The cover, the first layer, the second layer, and the third layer may be substantially transparent in some embodiments. A spacer may be disposed between the aperture in the cover and the first layer. Additionally or alternatively, a visually occlusive screen may be removable disposed over the cover. In some examples, the cover and the third layer may enclose the first layer and the second layer. In other examples, the first layer and the second layer may have an exposed perimeter.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
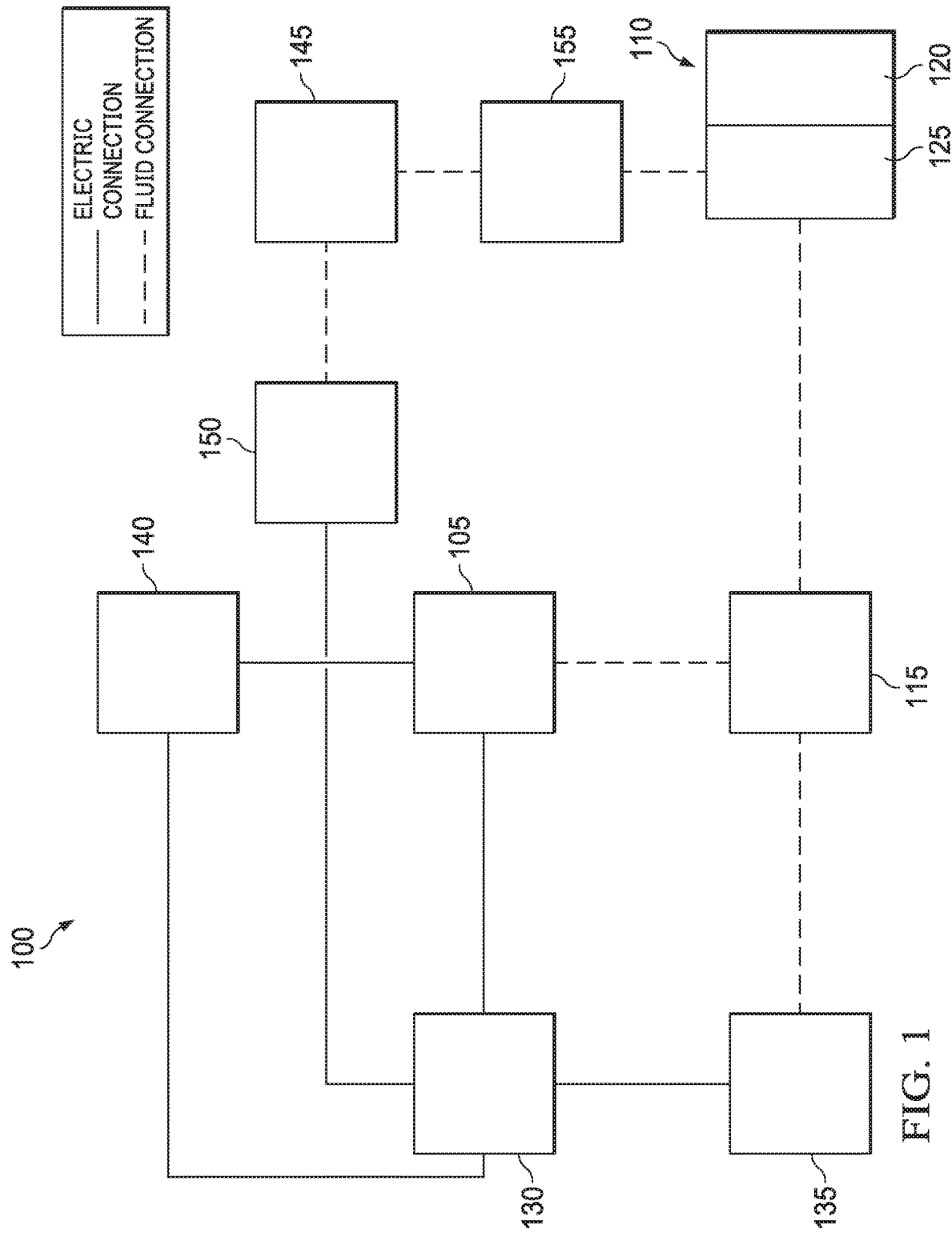
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source such as a positive-pressure source 150, a negative-pressure source such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage. Some containers may be re-usable, which can reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a non-porous polymer drape or film, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 g/m²/24 hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other types of fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

In some embodiments, the controller 130 may have a continuous pressure mode, in which the negative-pressure source 105 is operated to provide a constant target negative pressure for the duration of treatment or until manually deactivated. Additionally or alternatively, the controller may have an intermittent pressure mode. For example, the controller 130 can operate the negative-pressure source 105 to cycle between a target pressure and atmospheric pressure. For example, the target pressure may be set at a value of 135 mmHg for a specified period of time (e.g., 5 min), followed by a specified period of time (e.g., 2 min) of deactivation. The cycle can be repeated by activating the negative-pressure source 105, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time may be a value substantially equal to the initial rise time.

In some example dynamic pressure control modes, the target pressure can vary with time. For example, the target pressure may vary in the form of a triangular waveform, varying between a negative pressure of 50 and 135 mmHg with a rise time set at a rate of +25 mmHg/min. and a descent time set at −25 mmHg/min. In other embodiments of the therapy system 100, the triangular waveform may vary between negative pressure of 25 and 135 mmHg with a rise time set at a rate of +30 mmHg/min and a descent time set at −30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

In some embodiments, the controller 130 may receive and process data, such as data related to instillation solution provided to the tissue interface 120. Such data may include the type of instillation solution prescribed by a clinician, the volume of fluid or solution to be instilled to a tissue site ("fill volume"), and the amount of time prescribed for leaving solution at a tissue site ("dwell time") before applying a negative pressure to the tissue site. The fill volume may be, for example, between 10 and 500 mL, and the dwell time may be between one second to 30 minutes. The controller 130 may also control the operation of one or more components of the therapy system 100 to instill solution. For example, the controller 130 may manage fluid distributed from the solution source 145 to the tissue interface 120. In some embodiments, fluid may be instilled to a tissue site by applying a negative pressure from the negative-pressure source 105 to reduce the pressure at the tissue site, drawing solution into the tissue interface 120. In some embodiments, solution may be instilled to a tissue site by applying a positive pressure from the positive-pressure source 150 to move solution from the solution source 145 to the tissue interface 120. Additionally or alternatively, the solution source 145 may be elevated to a height sufficient to allow gravity to move solution into the tissue interface 120.

The controller 130 may also control the fluid dynamics of instillation by providing a continuous flow of solution or an intermittent flow of solution. Negative pressure may be applied to provide either continuous flow or intermittent flow of solution. The application of negative pressure may be implemented to provide a continuous pressure mode of operation to achieve a continuous flow rate of instillation solution through the tissue interface 120, or it may be implemented to provide a dynamic pressure mode of operation to vary the flow rate of instillation solution through the tissue interface 120. Alternatively, the application of negative pressure may be implemented to provide an intermittent mode of operation to allow instillation solution to dwell at the tissue interface 120. In an intermittent mode, a specific fill volume and dwell time may be provided depending, for example, on the type of tissue site being treated and the type of dressing being utilized. After or during instillation of solution, negative-pressure treatment may be applied. The controller 130 may be utilized to select a mode of operation and the duration of the negative pressure treatment before commencing another instillation cycle.

Figure 2:
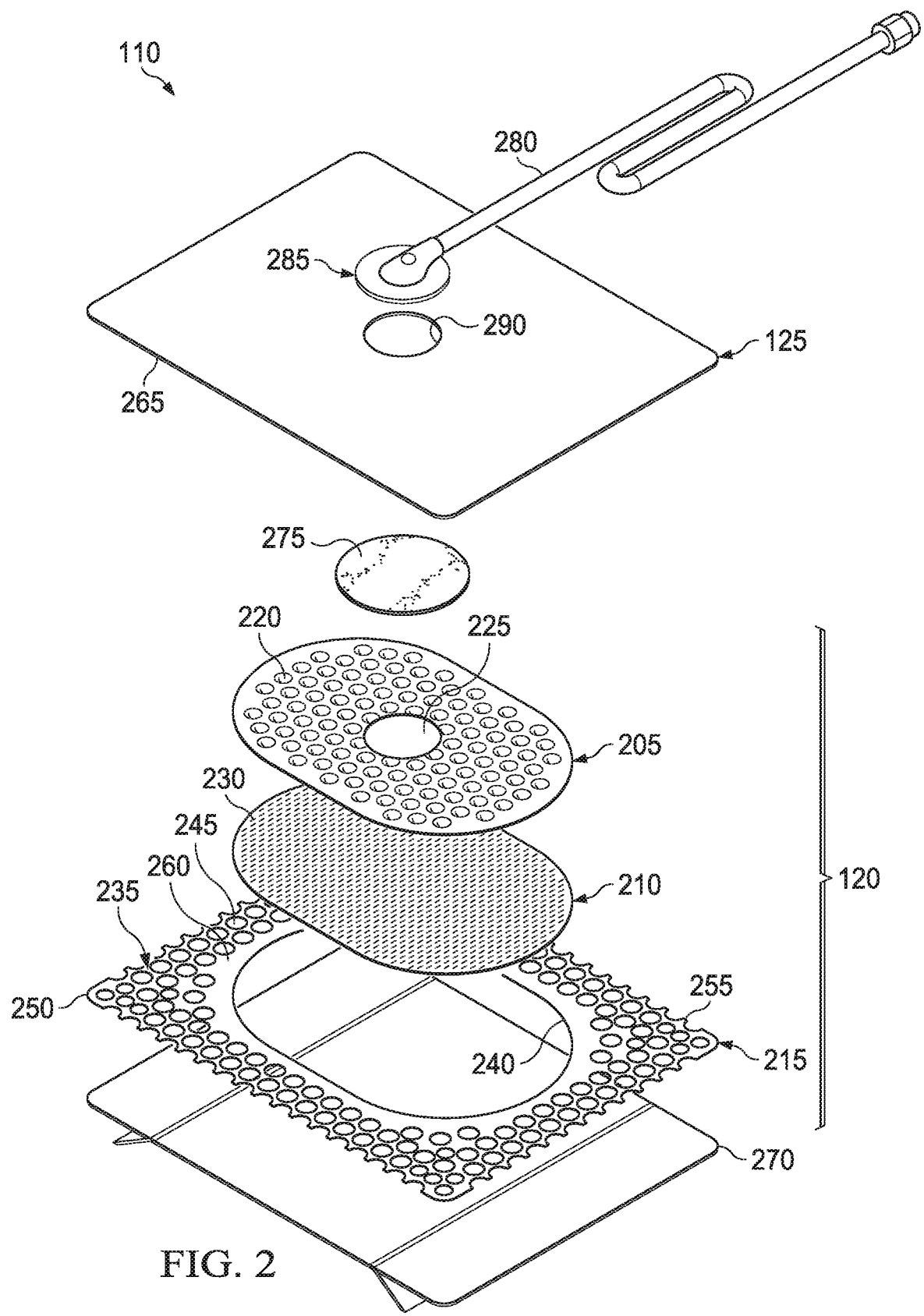
FIG. 2 is an assembly view of an example of a dressing that may be associated with some embodiments of the therapy system of FIG. 1.

FIG. 2 is an assembly view of an example of the dressing 110 of FIG. 1, illustrating additional details that may be associated with some embodiments in which the tissue interface 120 comprises more than one layer. In the example of FIG. 2, the tissue interface 120 comprises a first layer 205, a second layer 210, and a third layer 215. In some embodiments, the first layer 205 may be disposed adjacent to the second layer 210, and the third layer 215 may also be disposed adjacent to the second layer 210 opposite the first layer 205. For example, the first layer 205 and the second layer 210 may be stacked so that the first layer 205 is in contact with the second layer 210. The first layer 205 may also be bonded to the second layer 210 in some embodiments. In some embodiments, the second layer 210 may be coextensive with a face of the first layer 205. In some embodiments, at least some portion of the third layer 215 may be bonded to the second layer 210. The cover 125, the first layer 205, the second layer 210, and the third layer 215 may be substantially transparent or semi-transparent in some examples. For example, a transmission to white light of at least 80% may be suitable for some embodiments.

The first layer 205 generally comprises or consists essentially of a manifold or a manifold layer, which provides a means for collecting or distributing fluid across the tissue interface 120 under pressure. For example, the first layer 205 may be adapted to receive negative pressure from a source and distribute negative pressure across the tissue interface 120 through multiple pathways, which may have the effect of collecting fluid from across a tissue site and drawing the fluid toward the source. In some embodiments, the fluid path may be reversed or a secondary fluid path may be provided to facilitate delivering fluid, such as from a source of instillation solution, across the tissue interface 120.

In some illustrative embodiments, the pathways of the first layer 205 may be interconnected to improve distribution or collection of fluids. In some embodiments, the first layer 205 may comprise or consist essentially of a film of fluid-impermeable material having standoffs 220. Polyurethane is an example of a suitable fluid-impermeable material for some applications of the first layer 205. In some embodiments, the standoffs 220 may comprise a plurality of raised formations that extend above or below a plane of the first layer 205. Within each of the standoffs 220 may be an empty cavity, which may be open to the surrounding environment. For example, portions of a film of fluid-impermeable material that forms the first layer 205 may be shaped or formed into the standoffs 220. In some embodiments, the standoffs 220 may be in the form of small vacuum-formed regions of the film of the first layer 205. In some embodiments, each of the standoffs 220 may have a dome or hemispherical profile. Additionally or alternatively, the standoffs 220 may be in the form of raised blisters, bubbles, cells, bosses or other formations having different shapes, such as generally conical, cylindrical, tubular having a flattened or hemispherical end, or geodesic. The first layer 205 may further include at least one fluid passage, such as an aperture 225, which can allow fluid transfer through the first layer 205.

The thickness of the first layer 205 may also vary according to needs of a prescribed therapy. For example, the thickness of the first layer 205 may be decreased to relieve stress on other layers and to reduce tension on peripheral tissue. The thickness of the first layer 205 can also affect the conformability of the first layer 205. In some embodiments, the first layer 205 may comprise a flexible or elastic film having a thickness in a range of about 20 to 500 micrometers the standoffs 220 having a diameter of between 0.5 mm and 2.0 mm.

The second layer 210 may comprise or consist essentially of a means for controlling or managing fluid flow. In some embodiments, the second layer 210 may be a fluid control layer comprising or consisting essentially of a liquid-impermeable, elastomeric material. For example, the second layer 210 may comprise or consist essentially of a flexible or elastic polymer film, such as a polyurethane film. In some embodiments, the second layer 210 may comprise or consist essentially of the same material as the cover 125.

The second layer 210 may also have a smooth or matte surface texture in some embodiments. A glossy or shiny finish finer or equal to a grade B3 according to the SPI (Society of the Plastics Industry) standards may be particularly advantageous for some applications. In some embodiments, variations in surface height may be limited to acceptable tolerances. For example, the surface of the second layer 210 may have a substantially flat surface, with height variations limited to 0.2 millimeters over a centimeter. A thickness of about 50 microns to about 100 microns may be suitable for some examples.

In some embodiments, the second layer 210 may be embossed, which can create a pattern of contact areas with a manifolding effect. Examples of suitable patterns include taffeta, diamond, and weave patterns. Examples of materials suitable for embossing include polyurethane, polyethylene, polypropylene, polyamides, and their co-polymers. A thickness of about 200 microns to about 300 microns may be suitable for some examples.

In some embodiments, the second layer 210 may be hydrophobic. The hydrophobicity of the second layer 210 may vary, but may have a contact angle with water of at least ninety degrees in some embodiments. In some embodiments the second layer 210 may have a contact angle with water of no more than 150 degrees. For example, in some embodiments, the contact angle of the second layer 210 may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTÅ125, FTÅ200, FTÅ2000, and FTÅ4000 systems, all commercially available from First Ten Angstroms, Inc., of Portsmouth, VA, and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles herein represent averages of 5-9 measured values, discarding both the highest and lowest measured values. The hydrophobicity of the second layer 210 may be further enhanced with a hydrophobic coating of other materials, such as silicones and fluorocarbons, either as coated from a liquid, or plasma coated.

The second layer 210 may also be suitable for welding to other layers, including the first layer 205. For example, the second layer 210 may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene.

The area density of the second layer 210 may vary according to a prescribed therapy or application. In some embodiments, an area density of less than 40 grams per square meter may be suitable, and an area density of about 20-30 grams per square meter may be particularly advantageous for some applications.

In some embodiments, for example, the second layer 210 may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styrenics, silicones, fluoropolymers, and acetates. A thickness between 20 microns and 100 microns may be suitable for many applications. Films may be clear, colored, or printed. More polar films suitable for laminating to a polyethylene film include polyamide, co-polyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

As illustrated in the example of FIG. 2, the second layer 210 may have one or more fluid restrictions 230, which can be distributed uniformly or randomly across the second layer 210. The fluid restrictions 230 may be bi-directional and pressure-responsive. For example, each of the fluid restrictions 230 generally may comprise or consist essentially of an elastic passage that is normally unstrained to substantially reduce liquid flow, and can expand or open in response to a pressure gradient. In some embodiments, the fluid restrictions 230 may comprise or consist essentially of perforations in the second layer 210. Perforations may be formed by removing material from the second layer 210. For example, perforations may be formed by cutting through the second layer 210, which may also deform the edges of the perforations in some embodiments. In the absence of a pressure gradient across the perforations, the passages may be sufficiently small to form a seal or fluid restriction, which can substantially reduce or prevent liquid flow. Additionally or alternatively, one or more of the fluid restrictions 230 may be an elastomeric valve that is normally closed when unstrained to substantially prevent liquid flow, and can open in response to a pressure gradient. A fenestration in the second layer 210 may be a suitable valve for some applications. Fenestrations are generally a special case of perforations. Fenestrations may also be formed by removing material from the second layer 210, but the amount of material removed and the resulting dimensions of the fenestrations may be up to an order of magnitude less than perforations, and may not deform the edges.

For example, perforations may form slots in the second layer 210, and fenestrations may form slits, which are generally a special case of slots. In some embodiments of the fluid restrictions 230 may comprise or consist essentially of one or more slits, slots or combinations of slits and slots in the second layer 210. In some examples, the fluid restrictions 230 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications, and a tolerance of about 0.1 millimeter may also be acceptable. Such dimensions and tolerances may be achieved with a laser cutter, for example. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

The third layer 215 may comprise or consist essentially of a sealing layer or contact layer formed from a soft, pliable material suitable for providing a fluid seal with a tissue site, such as a suitable gel material, and may have a substantially flat surface. For example, the third layer 215 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. In some embodiments, the third layer 215 may have a thickness between about 200 microns (μm) and about 1000 microns (μm). In some embodiments, the third layer 215 may have a hardness between about 5 Shore OO and about 80 Shore OO. Further, the third layer 215 may be comprised of hydrophobic or hydrophilic materials.

In some embodiments, the third layer 215 may be a hydrophobic-coated material. For example, the third layer 215 may be formed by coating a spaced material, such as, for example, woven, nonwoven, molded, or extruded mesh with a hydrophobic material. The hydrophobic material for the coating may be a soft silicone, for example.

The third layer 215 may have a periphery 235 surrounding or around a treatment aperture 240, and apertures 245 in the periphery 235 disposed around the treatment aperture 240. The treatment aperture 240 may be complementary or correspond to a surface area of the first layer 205 in some examples. For example, the treatment aperture 240 may form a frame, window, or other opening around a surface of the first layer 205. The third layer 215 may also have corners 250 and edges 255. The corners 250 and the edges 255 may be part of the periphery 235. The third layer 215 may have an interior border 260 around the treatment aperture 240, which may be substantially free of the apertures 245, as illustrated in the example of FIG. 2. In some examples, as illustrated in FIG. 2, the treatment aperture 240 may be symmetrical and centrally disposed in the third layer 215, forming an open central window.

The apertures 245 may be formed by cutting, perforating, or by application of local RF or ultrasonic energy, for example, or by other suitable techniques for forming an opening or perforation in the third layer 215. The apertures 245 may have a uniform distribution pattern, or may be randomly distributed on the third layer 215. The apertures 245 in the third layer 215 may have many shapes, including circles, squares, stars, ovals, polygons, slits, complex curves, rectilinear shapes, triangles, for example, or may have some combination of such shapes.

Each of the apertures 245 may have uniform or similar geometric properties. For example, in some embodiments, each of the apertures 245 may be circular apertures, having substantially the same diameter. In some embodiments, each of the apertures 245 may have a diameter of about 1 millimeter to about 50 millimeters. In other embodiments, the diameter of each of the apertures 245 may be about 1 millimeter to about 20 millimeters.

In other embodiments, geometric properties of the apertures 245 may vary. For example, the diameter of the apertures 245 may vary depending on the position of the apertures 245 in the third layer 215. For example, in some embodiments, the apertures 245 disposed in the periphery 235 may have a diameter between about 5 millimeters and about 10 millimeters. A range of about 7 millimeters to about 9 millimeters may be suitable for some examples. In some embodiments, the apertures 245 disposed in the corners 250 may have a diameter between about 7 millimeters and about 8 millimeters.

At least one of the apertures 245 in the periphery 235 of the third layer 215 may be positioned at the edges 255 of the periphery 235, and may have an interior cut open or exposed at the edges 255 that is in fluid communication in a lateral direction with the edges 255. The lateral direction may refer to a direction toward the edges 255 and in the same plane as the third layer 215. As shown in the example of FIG. 2, the apertures 245 in the periphery 235 may be positioned proximate to or at the edges 255 and in fluid communication in a lateral direction with the edges 255. The apertures 245 positioned proximate to or at the edges 255 may be spaced substantially equidistant around the periphery 235 as shown in the example of FIG. 2. Alternatively, the spacing of the apertures 245 proximate to or at the edges 255 may be irregular.

As illustrated in the example of FIG. 2, the dressing 110 may further include an attachment device, such as an adhesive 265. The adhesive 265 may be, for example, a medically-acceptable, pressure-sensitive adhesive that extends about a periphery, a portion, or an entire surface of the cover 125. In some embodiments, for example, the adhesive 265 may be an acrylic adhesive having a coating weight between 25-65 grams per square meter (g.s.m.). Thicker adhesives, or combinations of adhesives, may be applied in some embodiments to improve the seal and reduce leaks. In some embodiments, such a layer of the adhesive 265 may be continuous or discontinuous. Discontinuities in the adhesive 265 may be provided by apertures or holes (not shown) in the adhesive 265. The apertures or holes in the adhesive 265 may be formed after application of the adhesive 265 or by coating the adhesive 265 in patterns on a carrier layer, such as, for example, a side of the cover 125. Apertures or holes in the adhesive 265 may also be sized to enhance the MVTR of the dressing 110 in some example embodiments.

As illustrated in the example of FIG. 2, in some embodiments, the dressing 110 may include a release liner 270 to protect the adhesive 265 prior to use. The release liner 270 may also provide stiffness to assist with, for example, deployment of the dressing 110. The release liner 270 may be, for example, a casting paper, a film, or polyethylene. Further, in some embodiments, the release liner 270 may be a polyester material such as polyethylene terephthalate (PET), or similar polar semi-crystalline polymer. The use of a polar semi-crystalline polymer for the release liner 270 may substantially preclude wrinkling or other deformation of the dressing 110. For example, the polar semi-crystalline polymer may be highly orientated and resistant to softening, swelling, or other deformation that may occur when brought into contact with components of the dressing 110, or when subjected to temperature or environmental variations, or sterilization. Further, a release agent may be disposed on a side of the release liner 270 that is configured to contact the second layer 210. For example, the release agent may be a silicone coating and may have a release factor suitable to facilitate removal of the release liner 270 by hand and without damaging or deforming the dressing 110. In some embodiments, the release agent may be a fluorocarbon or a fluorosilicone, for example. In other embodiments, the release liner 270 may be uncoated or otherwise used without a release agent.

The dressing 110 may additionally include a spacer manifold 275. In some embodiments, the spacer manifold 275 may have a structure that is similar to the first layer 205 with perforations between the standoffs. In other embodiments, the spacer manifold may comprise or consist essentially of a porous material having interconnected fluid pathways. Examples of suitable porous material that comprise or can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, the spacer manifold 275 may additionally or alternatively comprise projections that form interconnected fluid pathways. For example, in some examples the spacer manifold 275 may be molded to provide surface projections that define interconnected fluid pathways, or may have standoffs similar or analogous to the standoffs 220.

In some embodiments, the spacer manifold 275 may comprise or consist essentially of a reticulated foam. For example, a reticulated foam having a free volume of at least 90% may be suitable for many applications, and a foam having an average pore size in a range of 400-600 microns may be particularly suitable for some types of therapy. The tensile strength of the spacer manifold 275 may also vary. For example, the tensile strength of a foam may be increased for instillation of topical treatment solutions. The 25% compression load deflection of the spacer manifold 275 may be at least 0.35 pounds per square inch, and the 65% compression load deflection may be at least 0.43 pounds per square inch. In some embodiments, the tensile strength of the spacer manifold 275 may be at least 10 pounds per square inch. The spacer manifold 275 may have a tear strength of at least 2.5 pounds per inch. In some embodiments, the spacer manifold 275 may be a foam comprised of polyols such as polyester or polyether, isocyanate such as toluene diisocyanate, and polymerization modifiers such as amines and tin compounds. In some examples, the spacer manifold 275 may be a reticulated polyurethane foam such as used in GRANUFOAM™ dressing or V.A.C. VERA-FLO™ dressing, both available from KCI of San Antonio, Texas.

Other suitable materials for the spacer manifold 275 may include non-woven fabrics (Libeltex, Freudenberg), three-dimensional (3D) polymeric structures (molded polymers, embossed and formed films, and fusion bonded films [Supracore]), and mesh, for example.

In some examples, the spacer manifold 275 may include a 3D textile, such as various textiles commercially available from Baltex, Muller, and Heathcoates. A 3D textile of polyester fibers may be particularly advantageous for some embodiments. For example, the spacer manifold 275 may comprise or consist essentially of a three-dimensional weave of polyester fibers. In some embodiments, the fibers may be elastic in at least two dimensions. A puncture-resistant fabric of polyester and cotton fibers having a weight of about 650 grams per square meter and a thickness of about 1-2 millimeters may be particularly advantageous for some embodiments. Such a puncture-resistant fabric may have a warp tensile strength of about 330-340 kilograms and a weft tensile strength of about 270-280 kilograms in some embodiments. Another particularly suitable material may be a polyester spacer fabric having a weight of about 470 grams per square meter, which may have a thickness of about 4-5 millimeters in some embodiments. Such a spacer fabric may have a compression strength of about 20-25 kilopascals (at 40% compression).

FIG. 2 also illustrates one example of a fluid conductor 280 and a dressing interface 285. As shown in the example of FIG. 2, the fluid conductor 280 may be a flexible tube, which can be fluidly coupled on one end to the dressing interface 285. The dressing interface 285 may be an elbow connector, as shown in the example of FIG. 2, which can be placed over an aperture 290 in the cover 125 to provide a fluid path between the fluid conductor 280 and the tissue interface 120. The dressing interface 285 may be larger than the aperture 290, and in some embodiments may be coextensive with the spacer manifold 275.

As illustrated in the example of FIG. 2, the aperture 225, the spacer manifold 275, and the aperture 290 may be axially aligned in some embodiments, and the spacer manifold 275 may be disposed between the aperture 225 and the aperture 290. The aperture 225, the spacer manifold 275, and the aperture 290 may have similar shapes in some embodiments. In other embodiments, the spacer manifold 275 may have a shape similar to the second layer 210. The spacer manifold 275 is preferably larger than the aperture 225 and the aperture 290. In some examples, the spacer manifold 275 may have a thickness in a range of about 0.5 millimeters to about 10 millimeters.

One or more of the components of the dressing 110 may additionally be treated with an antimicrobial agent in some embodiments. For example, some embodiments of first layer 205, the second layer 210, or both may be a polymer coated or mixed with an antimicrobial agent. In other examples, the fluid conductor 280 may additionally or alternatively be treated with one or more antimicrobial agents. Suitable antimicrobial agents may include, for example, metallic silver, PHMB, iodine or its complexes and mixes such as povidone iodine, copper metal compounds, chlorhexidine, or some combination of these materials.

Additionally or alternatively, one or more of the components may be coated with a mixture that may include citric acid and collagen, which can reduce bio-films and infections. For example, the first layer 205 may be coated with such a mixture.

In some embodiments, the first layer 205 may be made from or coated with a material that can bind with and retain bacteria, which can prevent the bacteria from multiplying.

Figure 3:
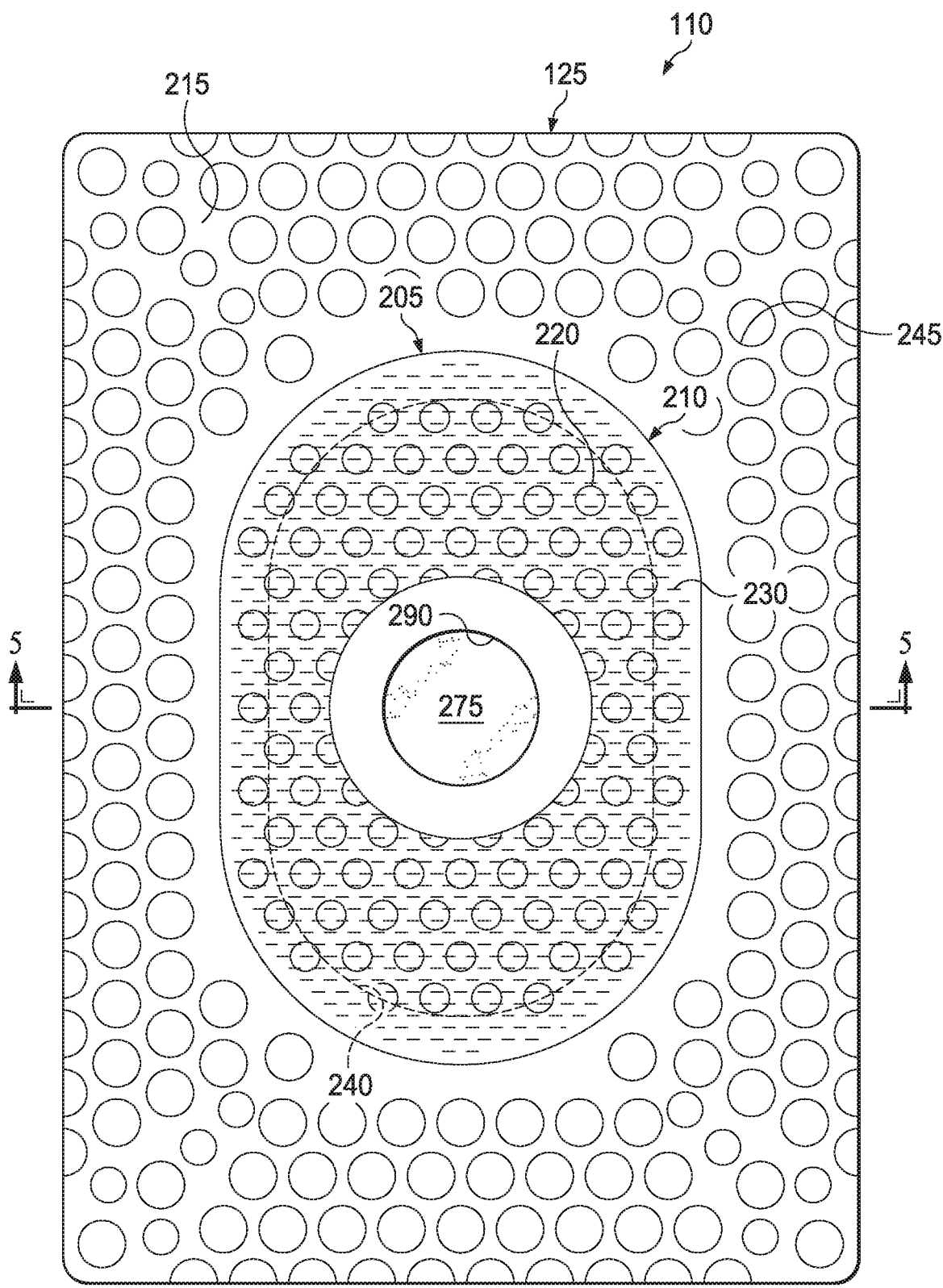
FIG. 3 is a top view of the dressing of FIG. 2, as assembled.

FIG. 3 is a top view of the dressing 110 in the example of FIG. 2, as assembled, illustrating additional details that may be associated with some embodiments. As illustrated in the example of FIG. 3, the cover 125 and the third layer 215 may have substantially the same perimeter shape and dimensions, so that the cover 125 and the third layer 215 are coextensive in some examples. The first layer 205 may be centrally disposed over the third layer 215, such as over the treatment aperture 240. The cover 125 may be disposed over the first layer 205 and the spacer manifold 275, with the aperture 290 aligned over the spacer manifold 275.

The cover 125 may be substantially transparent, allowing visibility of at least some of the apertures 245 and the fluid restrictions 230 in some embodiments. As illustrated in the example of FIG. 3, at least some of the fluid restrictions 230 may be offset from the standoffs 220. For example, the fluid restrictions 230 may be registered with the standoffs 220 so that a substantial portion of the fluid restrictions 230 do not align with the standoffs 220. In some embodiments, the standoffs 220 may not align with any of the fluid restrictions 230.

Figure 4:
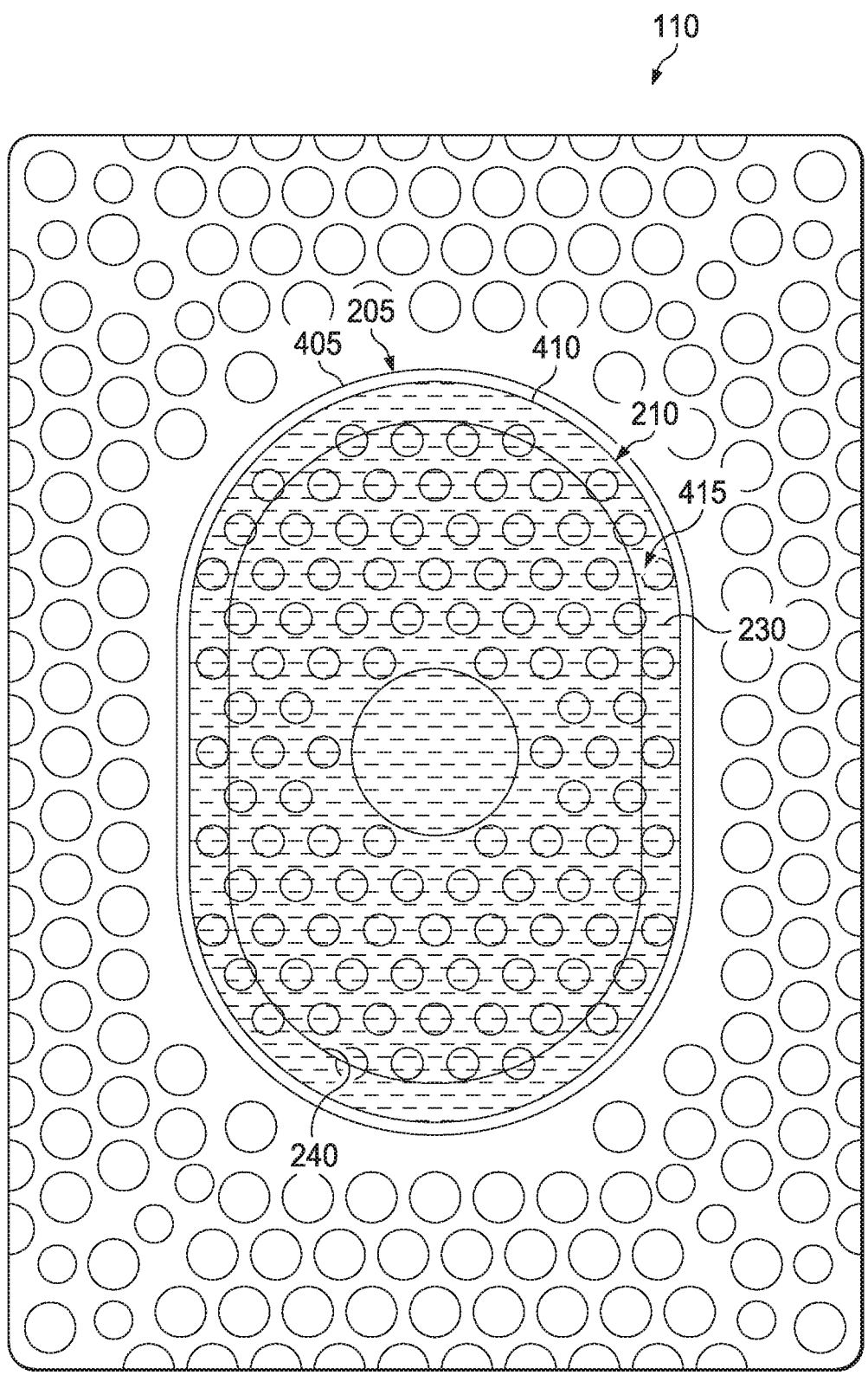
FIG. 4 is a bottom view of the dressing of FIG. 3.

FIG. 4 is a bottom view of the dressing 110 of FIG. 3, illustrating additional details that may be associated with some embodiments. The release liner 270 is removed in the example of FIG. 4. As illustrated in the example of FIG. 4, a substantial number of the fluid restrictions 230 may be aligned or otherwise exposed through the treatment aperture 240, and at least some portion of the first layer 205 may be disposed adjacent to the fluid restrictions 230 opposite the treatment aperture 240. In some embodiments, the first layer 205 and the second layer 210 may be substantially aligned with the treatment aperture 240, or may extend across the treatment aperture 240.

Additionally, the first layer 205 may have a first edge 405, and the second layer 210 may have a second edge 410. In some examples, the first edge 405 and the second edge 410 may have substantially the same shape so that adjacent faces of the first layer 205 and the second layer 210 are geometrically similar. The first edge 405 and the second edge 410 may also be congruent in some examples, so that adjacent faces of the first layer 205 and the second layer 210 are substantially coextensive and have substantially the same surface area. In the example of FIG. 4, the first edge 405 defines a larger face of the first layer 205 than the face of the second layer 210 defined by the second edge 410, and the larger face of the first layer 205 extends past the smaller face of the second edge 410.

The faces defined by the first edge 405, the second edge 410, or both may also be geometrically similar to the treatment aperture 240 in some embodiments, as illustrated in the example of FIG. 4, and may be larger than the treatment aperture 240. The third layer 215 may have an overlay margin 415 around the treatment aperture 240, which may have an additional adhesive disposed therein. As illustrated in the example of FIG. 4, the treatment aperture 240 may be an ellipse or a stadium in some embodiments. The treatment aperture 240 may have an area that is equal to about 20% to about 80% of the area of the third layer 215 in some examples. The treatment aperture 240 may also have an area that is equal to about 20% to about 80% of the area of a face of defined by the first edge 405 of the first layer 205. A width of about 90 millimeters to about 110 millimeters and a length of about 150 millimeters to about 160 millimeters may be suitable for some embodiments of the treatment aperture 240. For example, the width of the treatment aperture 240 may be about 100 millimeters, and the length may be about 155 millimeters. In some embodiments, a suitable width for the overlay margin 415 may be about 2 millimeters to about 3 millimeters. For example, the overlay margin 415 may be coextensive with an area defined between the treatment aperture 240 and the first edge 405, and the adhesive may secure the first layer 205, the second layer 210, or both to the third layer 215.

Figure 5:
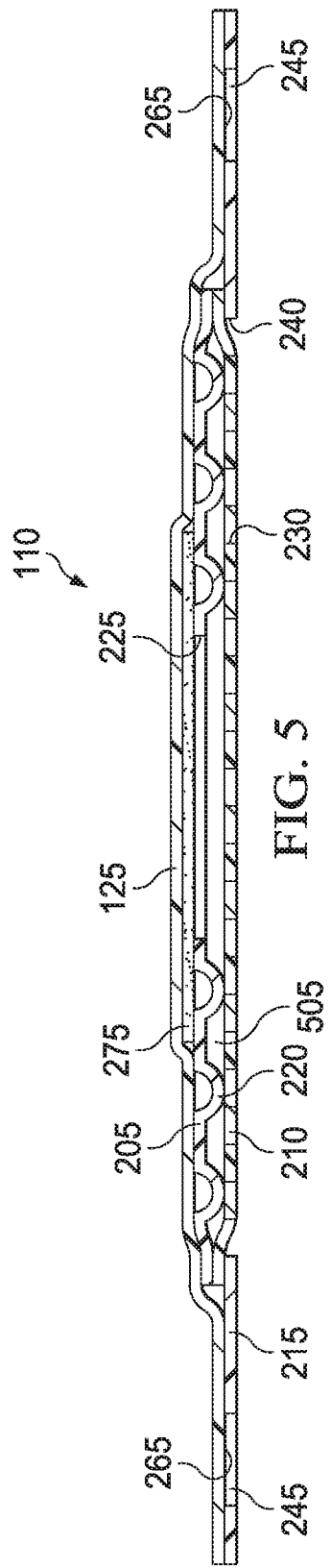
FIG. 5 is a section view of the dressing of FIG. 3.

FIG. 5 is a section view of the dressing 110 of FIG. 3, taken along line 5-5, illustrating additional details that may be associated with some embodiments. As illustrated in FIG. 5, the cover 125, the first layer 205, the second layer 210, the third layer 215, and the spacer manifold 275 may be assembled in a stacked relationship. The cover 125 may be coupled to the third layer 215 around the first layer 205 and the second layer 210, so that the cover 125 and the third layer 215 substantially enclose the first layer 205, the second layer 210, and the spacer manifold 275. The second layer 210 may be exposed through the treatment aperture 240, and at least some of the adhesive 265 can be exposed through the apertures 245.

The first layer 205 may be oriented so that the standoffs 220 are adjacent to the second layer 210, which can create a plurality of spaces 505 between the first layer 205 and the second layer 210. In some examples, the spaces 505 may form interconnected fluid pathways between the fluid restrictions 230 and the aperture 225. In the example of FIG. 5, the spacer manifold 275 is also disposed between the first layer 205 and the cover 125. As illustrated, the spacer manifold 275 may be disposed over the aperture 225, which can separate the cover 125 and the second layer 210 and provide additional fluid pathways.

As illustrated in the example of FIG. 5, some embodiments of the first layer 205 may be formed of a single sheet or film of fluid-impermeable material, which may have the standoffs 220 formed thereon. For example, the standoffs 220 may be formed in the first layer 205 by applying a vacuum to the film of fluid-impermeable material of the first layer 205. The standoffs may have dimensions that depend on the particular application of the dressing 110. For example, the first layer 205 may comprise a film having a thickness of about 500 microns, and each of the standoffs may have a height between approximately 1 millimeter and 4 millimeters. A width of between approximately 1 millimeter and 4 millimeters may also be suitable for some embodiments. In some embodiments, the standoffs 220 may measure approximately 3 millimeters in height and approximately 3 millimeters in diameter. Additionally, the standoffs 220 may be distributed across the first layer 205 in a uniform grid or array having a pitch of approximately 3.5 millimeters to about 4 millimeters. A pitch of about 3.75 millimeters may be particularly suitable for some examples. The spacing may be modified to alter flow characteristics and transparency, for example.

Figure 6:
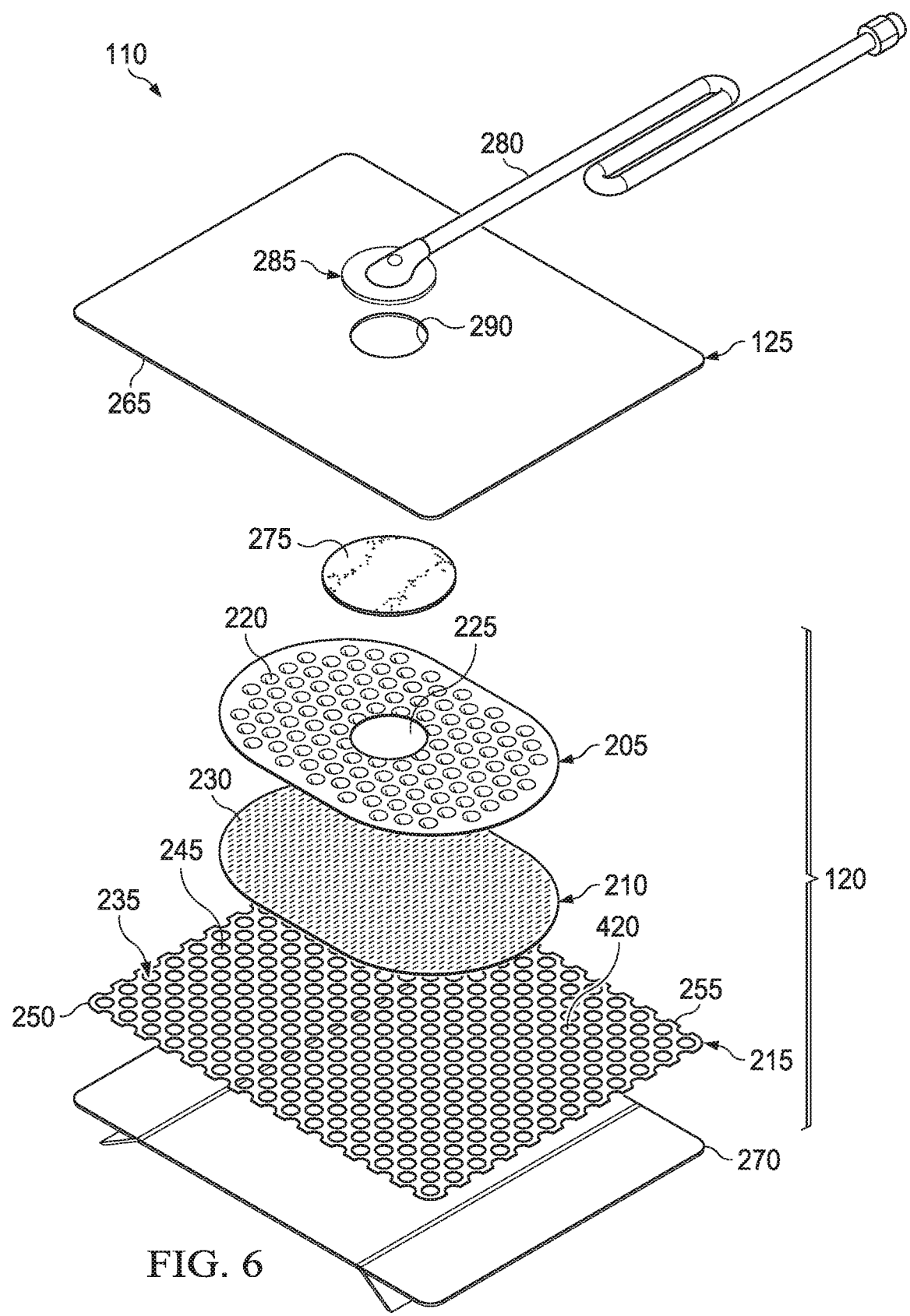
FIG. 6 is an assembly view of another example of a dressing that may be associated with some embodiments of the therapy system of FIG. 1.

FIG. 6 is an assembly view of another example of the dressing 110 of FIG. 1, illustrating additional details that may be associated with some embodiments. As illustrated in FIG. 6, some examples of the third layer 215 may not have the treatment aperture 240, and the apertures 245 may be distributed in a uniform pattern across the third layer 215.

Figure 7:
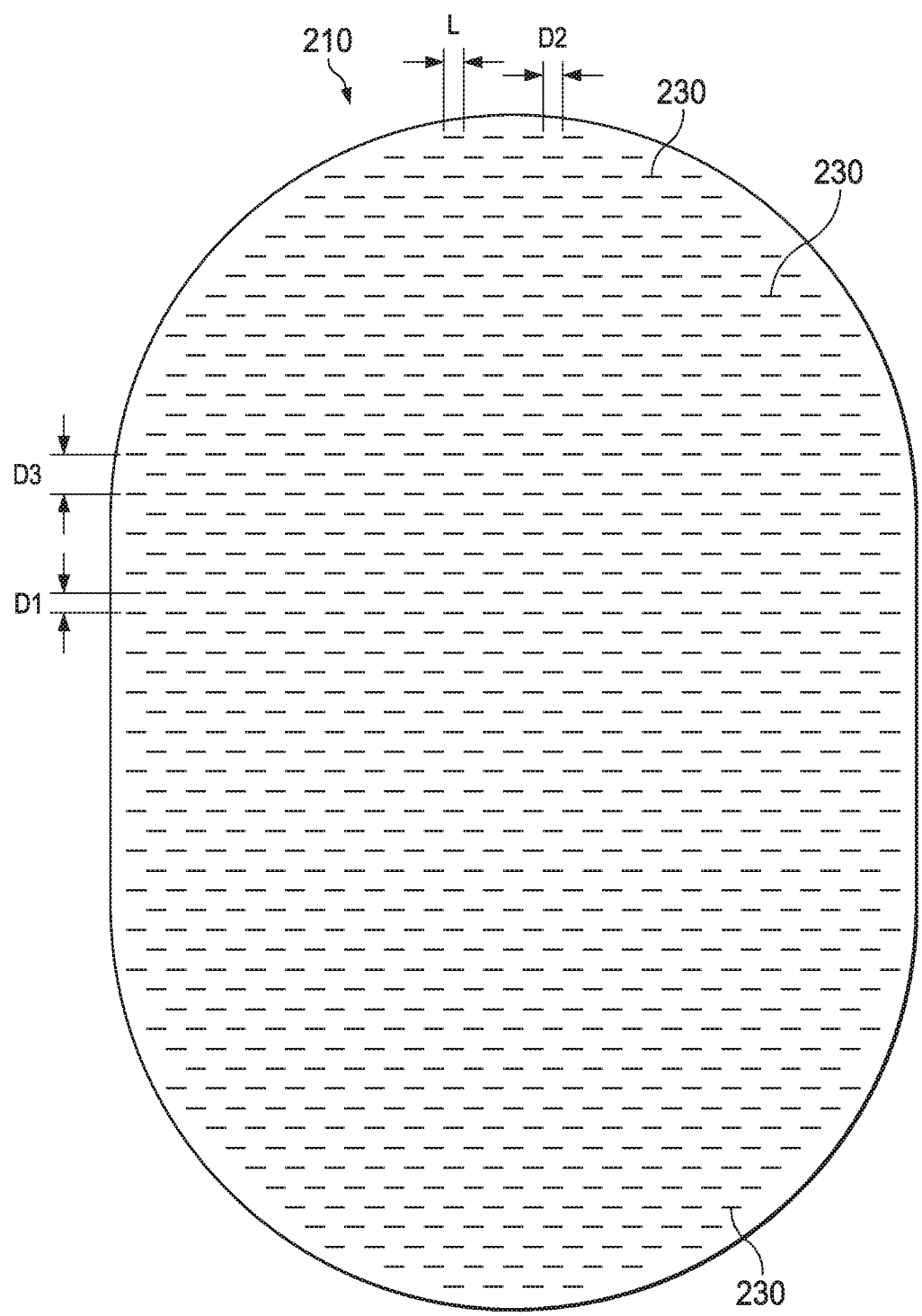
FIG. 7 is a schematic view of an example of a layer that may be associated with some dressings.

FIG. 7 is a schematic view of an example of the second layer 210, illustrating additional details that may be associated with some embodiments. As illustrated in the example of FIG. 7, the fluid restrictions 230 may each consist essentially of one or more slits having a length L. A length of about 3 millimeters may be particularly suitable for some embodiments. FIG. 7 additionally illustrates an example of a uniform distribution pattern of the fluid restrictions 230. In FIG. 7, the fluid restrictions 230 are substantially coextensive with the second layer 210, and are distributed across the second layer 210 in a grid of parallel rows and columns, in which the slits are also mutually parallel to each other. In some embodiments, the rows may be spaced a distance D1. A distance of about 3 millimeters on center may be suitable for some embodiments. The fluid restrictions 230 within each of the rows may be spaced a distance D2, which may be about 3 millimeters on center in some examples. The fluid restrictions 230 in adjacent rows may be aligned or offset in some embodiments. For example, adjacent rows may be offset, as illustrated in FIG. 7, so that the fluid restrictions 230 are aligned in alternating rows and separated by a distance D3, which may be about 6 millimeters in some embodiments. The spacing of the fluid restrictions 230 may vary in some embodiments to increase the density of the fluid restrictions 230 according to therapeutic requirements.

Figure 8:
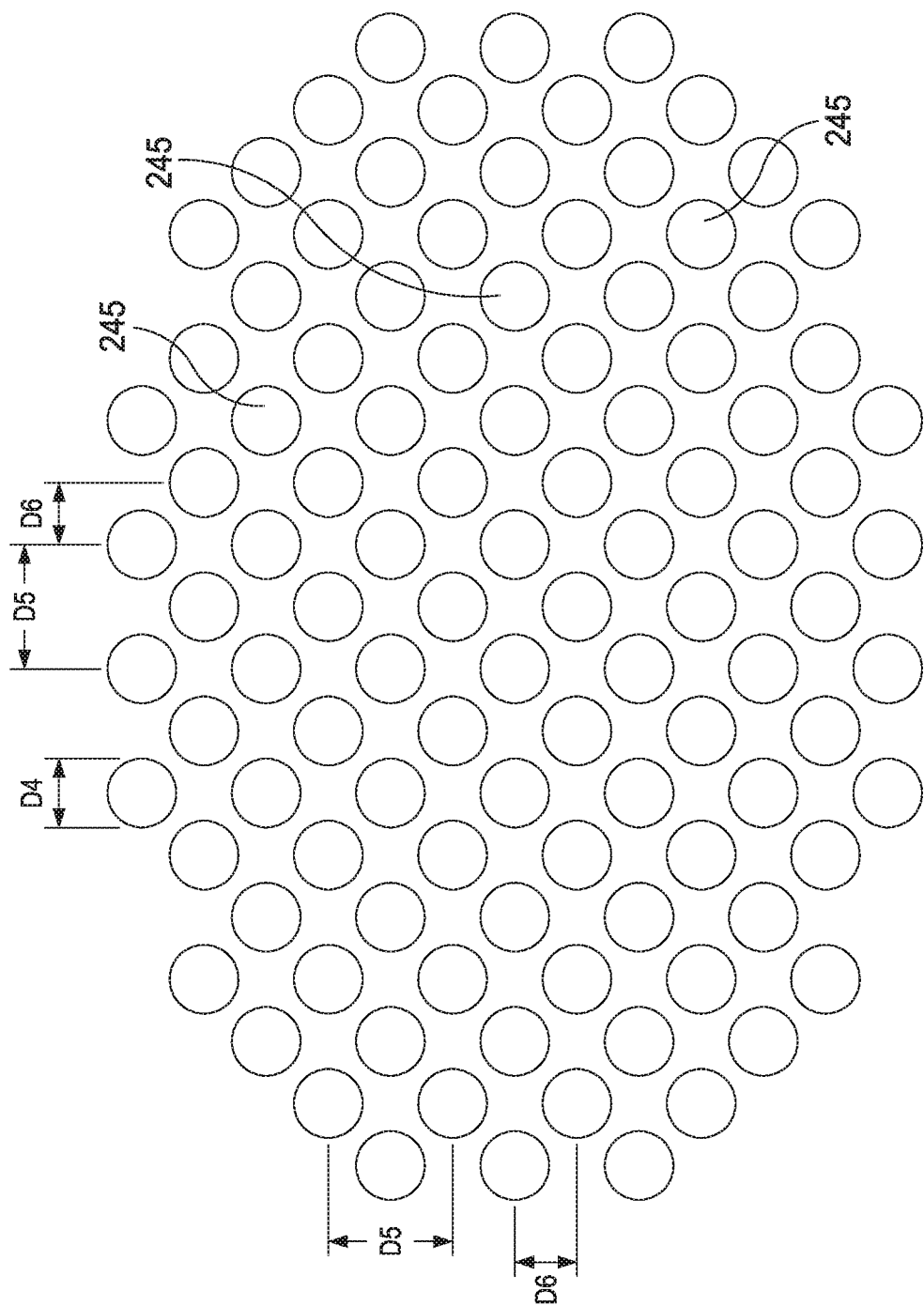
FIG. 8 is a schematic view of an example configuration of apertures that may be associated with a layer in some dressings.

FIG. 8 is a schematic view of an example configuration of the apertures 245, illustrating additional details that may be associated with some embodiments of the third layer 215. In the example of FIG. 8, the apertures 245 are generally circular and have a diameter D4, which may be about 6 millimeters to about 8 millimeters in some embodiments. A diameter D4 of about 7 millimeters may be particularly suitable for some embodiments. FIG. 8 also illustrates an example of a uniform distribution pattern of the apertures 245. In FIG. 8, the apertures 245 are distributed in a grid of parallel rows and columns. Within each row and column, the apertures 245 may be equidistant from each other, as illustrated in the example of FIG. 8. FIG. 8 illustrates one example configuration that may be particularly suitable for many applications, in which the apertures 245 are spaced a distance D5 apart along each row and column, with an offset of D6. In some examples, the distance D5 may be about 9 millimeters to about 10 millimeters, and the offset D6 may be about 8 millimeters to about 9 millimeters.

Figure 9:
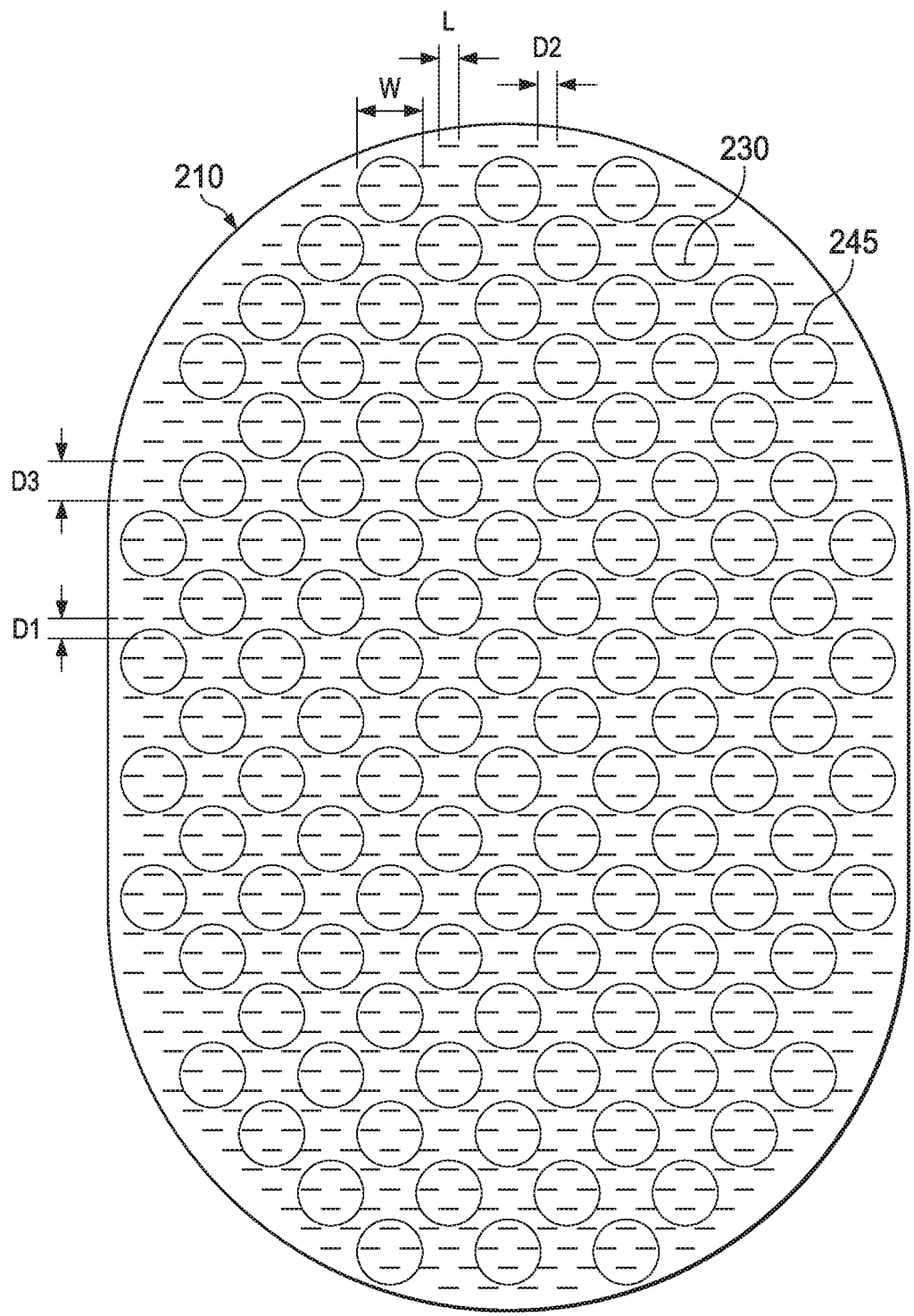
FIG. 9 is a schematic view of the apertures of FIG. 8 overlaid on the layer of FIG. 7.

FIG. 9 is a schematic view of the apertures 245 as configured in the example of FIG. 8 overlaid on the second layer 210 of FIG. 7, illustrating additional details that may be associated with some example embodiments of the tissue interface 120. For example, as illustrated in FIG. 9, more than one of the fluid restrictions 230 may be aligned, overlapping, in registration with, or otherwise fluidly coupled to the apertures 245 in some embodiments. In some embodiments, one or more of the fluid restrictions 230 may be only partially registered with the apertures 245. The apertures 245 in the example of FIG. 9 are generally sized and configured so that at least four of the fluid restrictions 230 are registered with each one of the apertures 245. In other examples, one or more of the fluid restrictions 230 may be registered with more than one of the apertures 245. For example, any one or more of the fluid restrictions 230 may be a perforation or a fenestration that extends across two or more of the apertures 245. Additionally or alternatively, one or more of the fluid restrictions 230 may not be registered with any of the apertures 245.

As illustrated in the example of FIG. 9, the apertures 245 may be sized to expose a portion of the second layer 210, the fluid restrictions 230, or both through the third layer 215. The apertures 245 in the example of FIG. 9 are generally sized to expose more than one of the fluid restrictions 230. Some or all of the apertures 245 may be sized to expose two or three of the fluid restrictions 230. In some examples, the length L of each of the fluid restrictions 230 may be substantially smaller than the width W of each of the apertures 245. More generally, the average dimensions of the fluid restrictions 230 are substantially smaller than the average dimensions of the apertures 245. In some examples, the apertures 245 may be elliptical, and the length of each of the fluid restrictions 230 may be substantially smaller than the major axis or the minor axis. In some embodiments, though, the dimensions of the fluid restrictions 230 may exceed the dimensions of the apertures 245, and the size of the apertures 245 may limit the effective size of the fluid restrictions 230 exposed to the lower surface of the dressing 110.

Figure 10:
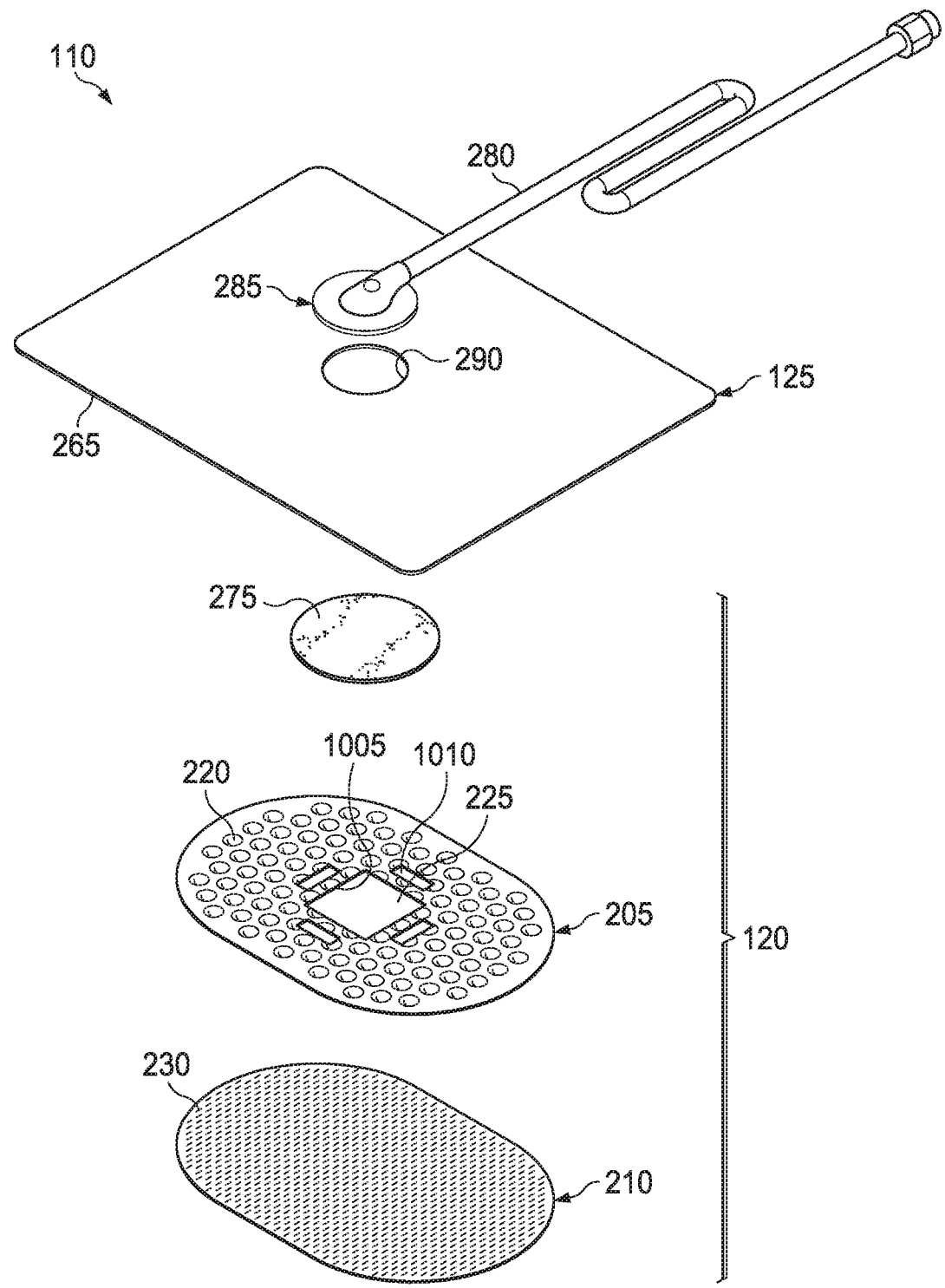
FIG. 10 is an assembly view of another example of a dressing that may be associated with some embodiments of the therapy system of FIG. 1.

FIG. 10 is an assembly view of another example of the dressing 110 of FIG. 1, illustrating additional details that may be associated with some embodiments. As illustrated in FIG. 10, some examples of the dressing 110 may not have the third layer 215. FIG. 10 also illustrates another example of the aperture 225. In the example of FIG. 10, the aperture 225 comprises a primary aperture 1005 and one or more auxiliary apertures 1010 around the primary aperture 1005. The primary aperture 1005 may be larger than the auxiliary apertures 1010 in some embodiments. For example, the primary aperture 1005 in FIG. 10 may have a width of about 10 millimeters, and each of the auxiliary apertures 1010 may have a width of about 3 millimeters.

Figure 11:
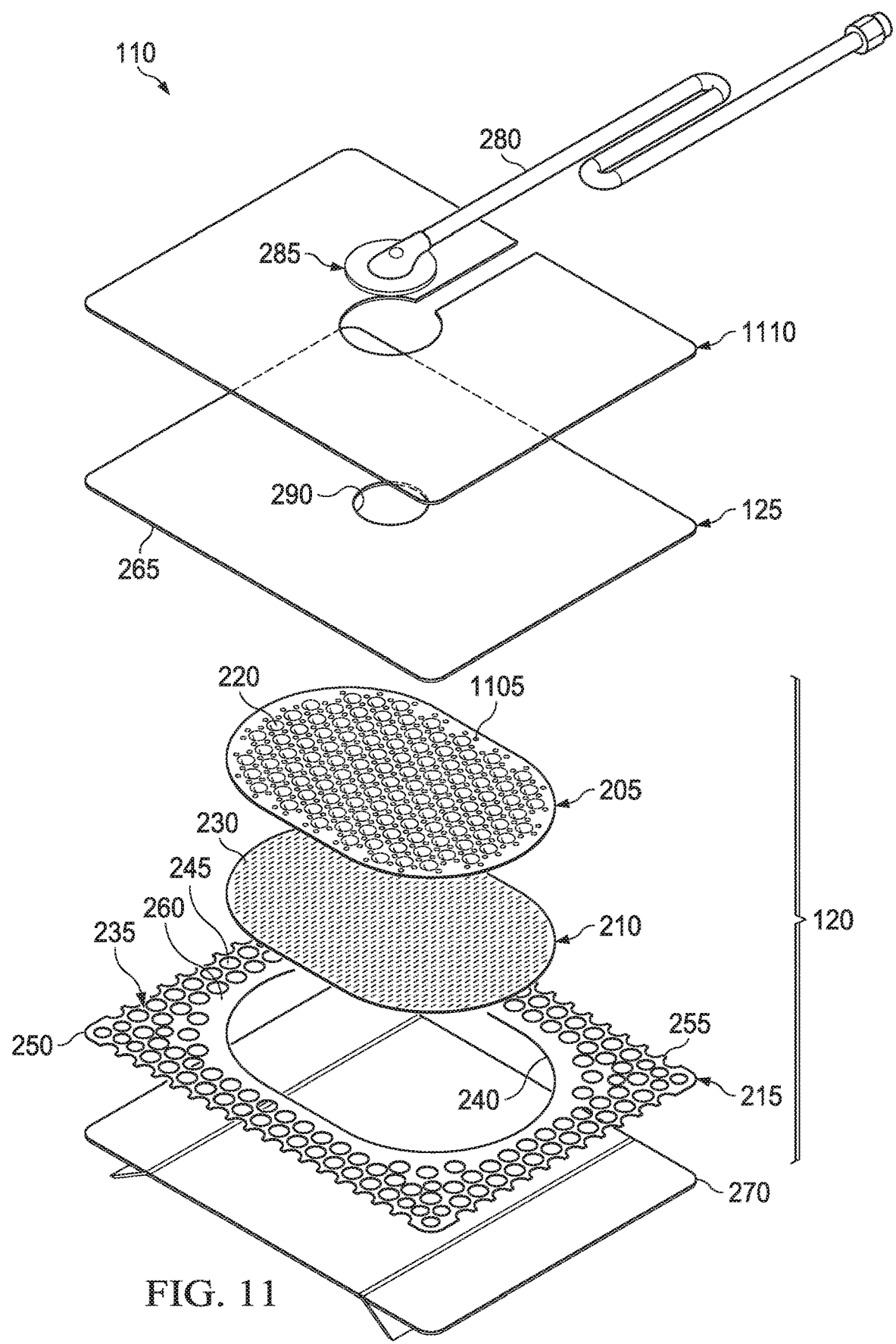
FIG. 11 is an assembly view of another example of a dressing that may be associated with some embodiments of the therapy system of FIG. 1.

FIG. 11 is an assembly view of another example of the dressing 110 of FIG. 1, illustrating additional details that may be associated with some embodiments. In some embodiments, the first layer 205 comprises a plurality fluid passages, in addition to or instead of the aperture 225. As shown in FIG. 11, the fluid passages may comprise apertures 1105 adjacent to the standoffs 220. In some examples, the apertures 1105 may be formed in the portions of the first layer 205 that are between the standoffs 220 and may extend through the first layer 205. The number of the apertures 1105 may vary depending on the type of application. The apertures 1105 may have different shapes, such as, for example, circular, elliptical, rectangular, or other irregular shape. The apertures 1105 may have a width, diameter, major axis, or length between about 0.5 mm and 1.5 mm. A diameter of about 1 millimeter may be suitable for some embodiments. In some example embodiments, the apertures 1105 may be formed by cutting or heat-perforating the first layer 205.

Additionally or alternatively, some embodiments of the dressing 110 may comprise a visual screen 1110, which can obscure a tissue site from patient view and be removed for assessment without disturbing the dressing 110. For example a suitable screen may comprise or consist essentially of highly-breathable polymer film that is opaque or at least partially optically occlusive. A visually occlusive polyurethane film may be suitable for some examples. In some embodiments, the visual screen may be assembled to the cover 125 and coated with a re-sealable adhesive, such as a pattern-coated silicone or polyurethane gel.

Individual components of the dressing 110 may be bonded or otherwise secured to one another with a solvent or non-solvent adhesive, or with heat bonding, for example, without adversely affecting fluid management. Further, the second layer 210 or the first layer 205 may be coupled to the interior border 260 or the overlay margin 415 of the third layer 215 in any suitable manner, such as with a weld or an adhesive, for example.

The cover 125, the first layer 205, the second layer 210, the third layer 215, the spacer manifold 275, or various combinations may be assembled before application or in situ. For example, the second layer 210 may be laminated to the first layer 205 in some embodiments. The cover 125 may be disposed over the first layer 205 and coupled to the third layer 215 around the first layer 205 in some embodiments. In some embodiments, one or more layers of the tissue interface 120 may be coextensive. For example, the second layer 210 may be cut flush with the edge of the first layer 205. In some embodiments, the dressing 110 may be provided as a composite dressing. For example, the third layer 215 may be coupled to the cover 125 to enclose the first layer 205 and the second layer 210, wherein the third layer 215 may be configured to face a tissue site. In other examples, the first layer 205, the second layer 210, and the third layer 215 may be coextensive, and the edges of each may be exposed around a perimeter of the tissue interface 120 to facilitate customization.

In use, the release liner 270 (if included) may be removed to expose a lower surface of the tissue interface 120. For example, in some embodiments removing the release liner 270 may expose the third layer 215. In some embodiments, the tissue interface 120 may be cut or trimmed as appropriate. The tissue interface 120 can be placed within, over, on, or otherwise proximate to a tissue site, particularly a surface tissue site and adjacent epidermis. In some applications, the treatment aperture 240 of the third layer 215 may be positioned adjacent to, proximate to, or covering a tissue site. In some applications, at least some portion of the second layer 210, the fluid restrictions 230, or both may be exposed to a tissue site through the treatment aperture 240, the apertures 245, or both. The periphery 235 of the third layer 215 may be positioned adjacent to or proximate to tissue around or surrounding the tissue site. The third layer 215 may be sufficiently tacky to hold the dressing 110 in position, while also allowing the dressing 110 to be removed or re-positioned without trauma to the tissue site.

Removing the release liner 270 can also expose the adhesive 265, and the cover 125 may be attached to an attachment surface, such as the periphery 235 or other area around the treatment aperture 240 and the first layer 205. The adhesive 265 may also be attached to epidermis peripheral to a tissue site, around the first layer 205 and the second layer 210. For example, the adhesive 265 may be in fluid communication with an attachment surface through the apertures 245 in at least the periphery 235 of the third layer 215. The adhesive 265 may also be in fluid communication with the edges 255 through the apertures 245 exposed at the edges 255.

Once the dressing 110 is in the desired position, the dressing 110 may be secured to the tissue site. In some embodiments, particularly if the tissue interface 120 has been cut for a custom size or shape, a cover may be bonded to an attachment surface around the edges of the tissue interface 120 to seal any exposed edges. Additionally or alternatively, in some embodiments the adhesive 265 may be pressed through the apertures 245 to bond the dressing 110 to the attachment surface. The apertures 245 at the edges 255 may permit the adhesive 265 to flow around the edges 255 for enhancing the adhesion of the edges 255 to an attachment surface.

In some embodiments, the apertures 245 may be sized to control the amount of the adhesive 265 exposed through the apertures 245. For a given geometry of the corners 250, the relative sizes of the apertures 245 may be configured to maximize the surface area of the adhesive 265 exposed and in fluid communication through the apertures 245 at the corners 250. For example, the edges 255 may intersect at substantially a right angle, or about 90 degrees, to define the corners 250. In some embodiments, the corners 250 may have a radius of about 10 millimeters. Further, in some embodiments, three of the apertures 245 may be positioned in a triangular configuration at the corners 250 to maximize the exposed surface area for the adhesive 265. In other embodiments, the size and number of the apertures 245 in the corners 250 may be adjusted as necessary, depending on the chosen geometry of the corners 250, to maximize the exposed surface area of the adhesive 265. Further, the apertures 245 at the corners 250 may be fully contained within the third layer 215, substantially precluding fluid communication in a lateral direction exterior to the corners 250. The apertures 245 at the corners 250 being fully contained within the third layer 215 may substantially preclude fluid communication of the adhesive 265 exterior to the corners 250, and may provide improved handling of the dressing 110 during deployment at a tissue site. Further, the exterior of the corners 250 being substantially free of the adhesive 265 may increase the flexibility of the corners 250 to enhance comfort.

In some embodiments, the bond strength of the adhesive 265 may vary based on the configuration of the third layer 215. For example, the bond strength may vary based on the size of the apertures 245. In some examples, the bond strength may be inversely proportional to the size of the apertures 245. Additionally or alternatively, the bond strength may vary in different locations, for example, if the size of the apertures 245 varies. For example, a lower bond strength in combination with larger apertures 245 may provide a bond comparable to a higher bond strength in locations having smaller apertures 245.

The geometry and dimensions of the tissue interface 120, the cover 125, or both may vary to suit a particular application or anatomy. For example, the geometry or dimensions of the tissue interface 120 and the cover 125 may be adapted to provide an effective and reliable seal against challenging anatomical surfaces, such as an elbow or heel, at and around a tissue site. Additionally or alternatively, the dimensions may be modified to increase the surface area for the third layer 215 to enhance the movement and proliferation of epithelial cells at a tissue site and reduce the likelihood of granulation tissue in-growth.

Thus, the dressing 110 can provide a sealed therapeutic environment proximate to a tissue site, substantially isolated from the external environment, and the negative-pressure source 105 can reduce the pressure in the sealed therapeutic environment. The treatment aperture 240 can provide an open area for delivery of negative pressure and passage of wound fluid through the second layer 210 and the first layer 205. Further, the dressing 110 may permit re-application or re-positioning, to correct air leaks caused by creases and other discontinuities in the dressing 110, for example. The ability to rectify leaks may increase the efficacy of the therapy and reduce power consumption in some embodiments.

If not already configured, the dressing interface 285 may be disposed over the aperture 290 and attached to the cover 125. The fluid conductor 280 may be fluidly coupled to the dressing interface 285 and to the negative-pressure source 105.

Negative pressure can be applied through the aperture 290 to the tissue interface 120. In some embodiments, the spacer manifold 275 may prevent the first layer 205 from being drawn or pushed into the aperture 290 and sealing off the tissue interface from the negative-pressure source 105. The standoffs 220 are preferably resistant to collapsing under therapeutic levels of negative pressure. In some examples, the cover 125 in combination with the standoffs 220 may effectively form closed cells that can increase the resistance to collapse.

Negative pressure applied through the tissue interface 120 can also create a negative pressure differential across the fluid restrictions 230 in the second layer 210, which can open or expand the fluid restrictions 230. For example, in some embodiments in which the fluid restrictions 230 may comprise substantially closed fenestrations through the second layer 210, a pressure gradient across the fenestrations can strain the adjacent material of the second layer 210 and increase the dimensions of the fenestrations to allow liquid movement through them, similar to the operation of a duckbill valve. Opening the fluid restrictions 230 can allow exudate and other liquid movement through the fluid restrictions 230 into the first layer 205. The first layer 205 can provide passage of negative pressure and wound fluid, which can be collected in the container 115.

Changes in pressure can also cause the first layer 205 to expand and contract. The second layer 210, the third layer 215, or both may protect the epidermis from irritation that could be caused by expansion, contraction, or other movement of the first layer 205. For example, in some embodiments, the overlay margin 415 may be disposed between the first layer 205 and epidermis around a tissue site. The second layer 210 and the third layer 215 can also substantially reduce or prevent exposure of a tissue site to the first layer 205, which can inhibit growth of tissue into the first layer 205. For example, the second layer 210 may cover the treatment aperture 240 to prevent direct contact between the first layer 205 and a tissue site.

If the negative-pressure source 105 is removed or turned off, the pressure differential across the fluid restrictions 230 can dissipate, allowing the fluid restrictions 230 to close and prevent exudate or other liquid from returning to the tissue site through the second layer 210.

In some applications, a filler may also be disposed between a tissue site and the third layer 215. For example, if the tissue site is a surface wound, a wound filler may be applied interior to the periwound, and the third layer 215 may be disposed over the periwound and the wound filler. In some embodiments, the filler may be a manifold, such as an open-cell foam. The filler may comprise or consist essentially of the same material as the first layer 205 or the spacer manifold 275 in some embodiments.

Additionally or alternatively, instillation solution or other fluid may be distributed to the dressing 110, which can increase the pressure in the tissue interface 120. The increased pressure in the tissue interface 120 can create a positive pressure differential across the fluid restrictions 230 in the second layer 210, which can open the fluid restrictions 230 to allow the instillation solution or other fluid to be distributed to the tissue site.

The systems, apparatuses, and methods described herein may provide significant advantages. For example, some dressings for negative-pressure therapy can require time and skill to be properly sized and applied to achieve a good fit and seal. In contrast, some embodiments of the dressing 110 provide a negative-pressure dressing that is simple to apply, reducing the time to apply and remove. In some embodiments, for example, the dressing 110 may be a fully-integrated negative-pressure therapy dressing that can be applied to a tissue site (including on the periwound) in one step, without being cut to size, while still providing or improving many benefits of other negative-pressure therapy dressings that require sizing. Such benefits may include good manifolding, beneficial granulation, minimal in-growth into the tissue interface, protection of the peripheral tissue from maceration, protection of the tissue site from shedding materials, and a low-trauma and high-seal bond. These characteristics may be particularly advantageous for surface wounds having moderate depth and medium-to-high levels of exudate. Some embodiments of the dressing 110 may remain on the tissue site for at least 5 days, and some embodiments may remain for at least 7 days. Antimicrobial agents in the dressing 110 may extend the usable life of the dressing 110 by reducing or eliminating infection risks that may be associated with extended use, particularly use with infected or highly exuding wounds.

Some embodiments of the dressing 110 may also provide a means to create micro-strain on a tissue site, and both primary and secondary manifolding of fluids. For example, some embodiments of the second layer 210 may be embossed to provide secondary manifolding, which can manifold small volumes of fluid at low pressures, and the first layer 205 can provide primary manifolding to move higher volumes of fluid at higher pressure. Additionally or alternatively, some embodiments of the dressing 110 can provide a substantially transparent structure, which can allow a tissue site to be observed or visualized without disrupting the integrity of the dressing 110 or treatment.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, one or more of the first layer 205, the second layer 210, or the third layer 215 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site with negative pressure, the dressing comprising:
   a cover comprising a first aperture;
   a first polymer film comprising a plurality of standoffs and a single second aperture axially aligned with the first aperture in the cover; and
   a second polymer film disposed adjacent to the standoffs in the first polymer film, the second polymer film including a plurality of fluid restrictions, wherein the plurality of standoffs form a plurality of spaces between the first polymer film and the second polymer film, and wherein the single second aperture is configured to provide the only fluid passage through the first polymer film to the plurality of spaces.

2. The dressing of claim 1, wherein the first polymer film and the second polymer film allow visualization of the tissue site.

3. The dressing of claim 1, wherein at least some of the standoffs are offset from the fluid restrictions.

4. The dressing of claim 1, wherein the second polymer film has a thickness in a range of about 50 microns to about 100 microns.

5. The dressing of claim 1, wherein the fluid restrictions are fenestrations in the second polymer film, wherein the fenestrations each have a length of about 2 millimeters to about 5 millimeters.

6. The dressing of claim 1, wherein the second polymer film has a thickness in a range of about 200 microns to about 300 microns.

7. The dressing of claim 1, wherein the first polymer film has a thickness of about 500 microns.

8. The dressing of claim 1, wherein each of the standoffs has a height in a range of about 1 millimeter to about 4 millimeters, wherein each of the standoffs has a width in a range of about 1 millimeter to about 4 millimeters, and wherein each of the standoffs have a pitch of about 3.5 millimeters to about 4 millimeters.

9. The dressing of claim 1, wherein the cover is disposed over the first polymer film.

10. The dressing of claim 1, further comprising a spacer disposed between the first aperture in the cover and the single second aperture in the first polymer film, the spacer axially aligned with the first aperture and the single second aperture.

11. The dressing of claim 1, further comprising a screen removably attached to the cover with a re-sealable adhesive, wherein the screen is opaque.

12. The dressing of claim 1, further comprising a layer of gel disposed adjacent to the second polymer film opposite the first polymer film, the layer of gel having perforations fluidly coupled with at least some of the fluid restrictions.

13. The dressing of claim 1, wherein the standoffs comprise blisters, bubbles, cells, bosses, or a combination thereof.

14. The dressing of claim 1, further comprising:
a third layer comprising a treatment aperture;
wherein the cover, the first polymer film, the second polymer film, and the third layer are assembled in a stacked relationship with the first polymer film and the second polymer film between the cover and the third layer, and wherein at least some of the fluid restrictions are exposed through the treatment aperture.

15. The dressing of claim 14, wherein the treatment aperture forms a frame around at least some of the fluid restrictions.

16. The dressing of claim 14, wherein the cover, the first polymer film, the second polymer film, and the third layer are substantially transparent.

17. The dressing of claim 14, wherein the cover and the third layer enclose the first polymer film and the second polymer film.

18. An apparatus for treating a tissue site with negative pressure, the apparatus comprising:
a dressing according to claim 1; and
a negative-pressure source fluidly coupled to the dressing.

19. A method of treating a tissue site with negative pressure, the method comprising:
applying the dressing of claim 1 to the tissue site;
applying negative pressure to the tissue site through the dressing; and
observing the tissue site through the dressing.

20. A method of treating a tissue site with negative pressure, the method comprising:
applying the dressing of claim 1 to the tissue site, the dressing comprising a screen configured to obscure the tissue site;
applying negative pressure to the tissue site through the dressing;
removing the screen;
observing the tissue site through the dressing; and
replacing the screen to obscure the tissue site.

* * * * *